United States Patent
Jervis (10) Patent No.: US 8,062,333 B2
(45) Date of Patent: Nov. 22, 2011

(54) SUTURE RETAINER WITH MULTIPLE CIRCUMFERENTIALLY SPACED ATTACHMENT POINTS AND SUTURE RETENTION METHOD

(75) Inventor: James E. Jervis, Atherton, CA (US)

(73) Assignee: Anpa Medical, Inc., San Mateo, CA (US)

( * ) Notice: Subject to any disclaimer, the term of this patent is extended or adjusted under 35 U.S.C. 154(b) by 274 days.

(21) Appl. No.: 11/061,128

(22) Filed: Feb. 17, 2005

(65) Prior Publication Data

US 2006/0184200 A1    Aug. 17, 2006

(51) Int. Cl.
*A61B 17/04* (2006.01)
(52) U.S. Cl. ........................................ 606/232
(58) Field of Classification Search ................. 606/148, 606/232; 112/231, 279; 24/130
See application file for complete search history.

(56) References Cited

U.S. PATENT DOCUMENTS

| 516,555 | A | * | 3/1894 | Smith ........................ 24/129 R |
| 551,032 | A | | 12/1895 | Hemphill, Jr. |
| 1,470,261 | A | * | 10/1923 | Harrington ..................... 24/127 |
| 3,498,575 | A | | 3/1970 | Downing |
| 3,574,900 | A | | 4/1971 | Emery |

(Continued)

FOREIGN PATENT DOCUMENTS

GB    2365351 B    11/2002

(Continued)

OTHER PUBLICATIONS

James E. Jervis, U.S. Appl. No. 11/061,320, entitled "Suture retainer with suture guide and method of using a suture retainer with a suture guide," filed Feb. 17, 2005.

(Continued)

*Primary Examiner* — Ryan Severson
(74) *Attorney, Agent, or Firm* — Ryan Kromholz & Manion, S.C.

(57) ABSTRACT

The suture retainer according to one aspect of the invention has a retainer body and a plurality of suture attachment mechanisms spaced circumferentially about the retainer body, each of the suture attachment mechanisms (such as a pair of teeth) being adapted to hold a suture strand at a discrete attachment point. Another aspect of the invention provides a method of securing a suture in a suture retainer, including the following steps: providing a suture retainer having a retainer body and a plurality of suture attachment mechanisms spaced circumferentially about the retainer body; and attaching a suture strand to the retainer body at each of the suture attachment mechanisms. Yet another aspect of the invention provides a suturing method including the steps of: attaching a first end of a suture strand to a suture retainer; contacting a tissue contact portion of the suture strand with tissue to be sutured, the tissue contact portion being disposed between the first end of the suture strand and a second end of the suture strand; and attaching the second end of the suture strand to the suture retainer at a plurality of suture attachment points spaced circumferentially about the suture retainer.

15 Claims, 5 Drawing Sheets

U.S. PATENT DOCUMENTS

| | | | |
|---|---|---|---|
| 3,988,810 A | 11/1976 | Emery | |
| 4,416,503 A | 11/1983 | Hayes | |
| 4,750,492 A | 6/1988 | Jacobs | |
| 4,787,660 A | 11/1988 | Mrazek | |
| 4,811,735 A | 3/1989 | Nash et al. | |
| 4,896,403 A | 1/1990 | Vouros | |
| 4,950,285 A | 8/1990 | Wilk | |
| 4,969,892 A * | 11/1990 | Burton et al. | 606/218 |
| 5,026,363 A | 6/1991 | Pratt | |
| 5,037,433 A | 8/1991 | Wilk et al. | |
| 5,068,495 A | 11/1991 | Dahl-Bettermann-Winand | |
| 5,078,731 A | 1/1992 | Hayhurst | |
| 5,123,913 A | 6/1992 | Wilk et al. | |
| 5,123,914 A | 6/1992 | Cope | |
| 5,156,610 A | 10/1992 | Reger | |
| 5,160,339 A | 11/1992 | Chen et al. | |
| 5,171,251 A | 12/1992 | Bregen et al. | |
| 5,190,561 A | 3/1993 | Graber | |
| 5,211,651 A | 5/1993 | Reger et al. | |
| 5,219,359 A | 6/1993 | McQuilkin et al. | |
| 5,234,449 A | 8/1993 | Bruker et al. | |
| 5,258,015 A * | 11/1993 | Li et al. | 606/232 |
| 5,282,832 A | 2/1994 | Toso et al. | |
| 5,330,442 A | 7/1994 | Green et al. | |
| 5,372,604 A | 12/1994 | Trott | |
| 5,376,101 A | 12/1994 | Green et al. | |
| 5,383,905 A | 1/1995 | Golds et al. | |
| 5,391,173 A | 2/1995 | Wilk | |
| 5,405,359 A | 4/1995 | Pierce | |
| 5,409,499 A | 4/1995 | Yi | |
| 5,411,522 A | 5/1995 | Trott | |
| 5,413,585 A | 5/1995 | Pagedas | |
| 5,441,224 A | 8/1995 | Ludwig | |
| 5,472,452 A | 12/1995 | Trott | |
| 5,474,572 A | 12/1995 | Hayhurst | |
| 5,500,001 A | 3/1996 | Trott | |
| 5,501,683 A | 3/1996 | Trott | |
| 5,501,696 A | 3/1996 | Trott | |
| 5,514,159 A | 5/1996 | Matula et al. | |
| 5,520,703 A | 5/1996 | Essig et al. | |
| 5,522,120 A | 6/1996 | Brinning | |
| 5,537,776 A | 7/1996 | Gilard, Sr. | |
| 5,626,590 A * | 5/1997 | Wilk | 606/148 |
| 5,630,824 A | 5/1997 | Hart | |
| 5,643,295 A | 7/1997 | Yoon | |
| 5,643,297 A | 7/1997 | Nordgren et al. | |
| 5,643,298 A | 7/1997 | Nordgren et al. | |
| 5,645,553 A | 7/1997 | Kolesa et al. | |
| 5,649,940 A | 7/1997 | Hart et al. | |
| 5,669,935 A | 9/1997 | Rosenman et al. | |
| 5,681,351 A | 10/1997 | Jamiolkowski et al. | |
| 5,683,418 A | 11/1997 | Luscombe et al. | |
| 5,725,556 A | 3/1998 | Moser et al. | |
| 5,735,877 A | 4/1998 | Pagedas | |
| 5,741,301 A | 4/1998 | Pagedas | |
| 5,782,864 A | 7/1998 | Lizardi | |
| 5,802,679 A * | 9/1998 | Neeley | 24/130 |
| 5,806,452 A | 9/1998 | Benoit | |
| 5,810,853 A * | 9/1998 | Yoon | 606/151 |
| 5,810,882 A | 9/1998 | Bolduc et al. | |
| 5,814,052 A | 9/1998 | Nakao et al. | |
| 5,845,645 A | 12/1998 | Bonutti | |
| 5,879,371 A | 3/1999 | Gardiner et al. | |
| 5,895,393 A | 4/1999 | Pagedas | |
| 5,906,620 A | 5/1999 | Nakao et al. | |
| 5,948,001 A | 9/1999 | Larsen | |
| 5,957,903 A | 9/1999 | Mirzaee et al. | |
| 5,961,538 A | 10/1999 | Pedlick et al. | |
| 5,980,524 A | 11/1999 | Justin et al. | |
| 6,010,525 A | 1/2000 | Bonutti et al. | |
| 6,015,428 A | 1/2000 | Pagedas | |
| 6,039,176 A | 3/2000 | Wright | |
| 6,066,160 A | 5/2000 | Colvin et al. | |
| 6,074,395 A | 6/2000 | Trott et al. | |
| 6,080,184 A | 6/2000 | Peters et al. | |
| 6,096,060 A | 8/2000 | Fitts et al. | |
| 6,106,545 A | 8/2000 | Egan | |
| 6,143,017 A | 11/2000 | Thal | |
| 6,149,669 A | 11/2000 | Li | |
| 6,159,234 A | 12/2000 | Bonutti et al. | |
| 6,163,936 A | 12/2000 | Benoit | |
| 6,231,592 B1 | 5/2001 | Bonutti et al. | |
| 6,296,659 B1 | 10/2001 | Foerster | |
| 6,319,271 B1 | 11/2001 | Schwartz et al. | |
| 6,432,123 B2 | 8/2002 | Schwartz et al. | |
| 6,464,713 B2 | 10/2002 | Bonutti | |
| 6,475,229 B1 | 11/2002 | Pagedas | |
| 6,475,230 B1 | 11/2002 | Bonutti et al. | |
| 6,527,794 B1 | 3/2003 | McDevitt et al. | |
| 6,527,795 B1 | 3/2003 | Lizardi | |
| 6,533,795 B1 | 3/2003 | Tran et al. | |
| 6,551,330 B1 | 4/2003 | Bain et al. | |
| 6,592,609 B1 | 7/2003 | Bonutti | |
| 6,605,096 B1 | 8/2003 | Ritchart | |
| 6,626,917 B1 | 9/2003 | Craig | |
| 6,641,597 B2 | 11/2003 | Burkhart et al. | |
| 6,660,023 B2 | 12/2003 | McDevitt et al. | |
| 6,699,263 B2 | 3/2004 | Cope | |
| 6,896,686 B2 | 5/2005 | Weber | |
| 6,902,545 B2 | 6/2005 | Bertolero et al. | |
| 6,997,189 B2 | 2/2006 | Biggs et al. | |
| 2001/0051816 A1 | 12/2001 | Enzerink et al. | |
| 2002/0111653 A1 | 8/2002 | Foerster | |
| 2003/0195562 A1 | 10/2003 | Collier et al. | |
| 2004/0044366 A1* | 3/2004 | Bonutti et al. | 606/232 |
| 2004/0220617 A1 | 11/2004 | Pedlick et al. | |
| 2004/0260344 A1 | 12/2004 | Lyons et al. | |
| 2004/0260345 A1 | 12/2004 | Foerster | |
| 2005/0177181 A1 | 8/2005 | Kagan et al. | |
| 2006/0004410 A1 | 1/2006 | Nobis et al. | |

FOREIGN PATENT DOCUMENTS

| | | |
|---|---|---|
| GB | 2337934 B | 2/2003 |
| GB | 2379885 B | 5/2003 |

OTHER PUBLICATIONS

James E. Jervis, et al. U.S. Appl. No. 11/380,573, entitled "Wedge operated retainer device and methods," filed Apr. 27, 2006.

James E. Jervis, et al. U.S. Appl. No. 11/249,008, entitled "Helical retainer, tool for using the helical retainer, and methods," filed Oct. 11, 2005.

PCT Search Report of Aug. 24, 2007 regarding Application No. pct/us06/27929.

USPTO Office Action dated Jul. 26, 2007 regarding U.S. Appl. No. 11/061,320, 6 pages.

* cited by examiner

SUTURE RETAINER WITH MULTIPLE CIRCUMFERENTIALLY SPACED ATTACHMENT POINTS AND SUTURE RETENTION METHOD

BACKGROUND OF THE INVENTION

The invention relates generally to suture retainers and methods of using suture retainers. In particular, the invention relates to suture retainers that hold a suture strand at a plurality of circumferentially spaced points about the suture retainer.

Sutures are used for a variety of surgical purposes, such as approximation of tissue and ligation of tissue. Most generally, when placing sutures, the strand of suture material to be used has a needle affixed to one end. The needle is passed through the tissue to be approximated or ligated, forming a stitch. The stitch is then tensioned appropriately, and the two ends of the suture, the needle end and the non-needle end, are knotted to retain the desired tension in the stitch. Sometimes the ends are knotted together; in other instances they may be stoppered separately, often with the aid of a clip or other device to form resistance to passage through tissue. While forming knots in suture during open surgery is a simple matter, forming knots in suture during endoscopic surgery can be very difficult.

Suture retainers may be used in place of suture knots to prevent passage of a suture end into and through tissue and to maintain the tension applied to the suture material during the suturing procedure. Suture clips and other suture retainers are described in the following publications: U.S. Pat. Nos. 5,234,449; 5,383,905; 5,391,173; 5,643,295; 5,645,553; 5,735,877; 5,845,645; 5,895,393; 6,015,428; 6,066,160; 6,231,592; and 6,432,123.

SUMMARY OF THE INVENTION

The present invention provides a suture retainer with multiple circumferentially spaced attachment points. The invention also provides a suture retainer with a suture guide mechanism adapted to maintain an angle between a suture strand and a suture attachment mechanism. While the suture retainer of this invention can be used in conventional open surgeries or external surgeries, the invention is particularly useful for endoscopic suturing.

The suture retainer according to one aspect of the invention has a retainer body and a plurality of suture attachment mechanisms spaced circumferentially about the retainer body, each of the suture attachment mechanisms (such as a pair of teeth) being adapted to hold a suture strand at a discrete attachment point. In some embodiments, each suture attachment mechanism is adapted to releasably hold the suture strand.

In some embodiments of the invention, the suture retainer also has a suture guide mechanism, such as a projection from the retainer body, adapted to maintain an angle between the suture strand and one of the suture attachment mechanisms. The suture guide mechanism may be adapted to be a first contact point of the suture strand with the suture retainer.

In some embodiments, the suture attachment mechanisms are needle-end suture attachment mechanisms, with the suture retainer also including a non-needle-end suture attachment mechanism adapted to hold a non-needle-end of the suture strand. The non-needle-end suture attachment mechanism may be disposed radially inward from each of the needle-end suture attachment mechanisms. Also, in some embodiments, the retainer body has a first member and a second member, with at least a portion of the second member being adapted to be inserted into the first member to form the non-needle-end suture attachment mechanism, such as a slot in the second member which interacts with the first member to hold the non-needle-end of the suture strand. The suture retainer may also have an alignment mechanism adapted to orient the second member with respect to the first member. In some embodiments, the suture retainer also has a movable connection between the first member and the second member, and in some embodiments the suture retainer has a snap connection between the first member and the second member. In some embodiments, a suture guide mechanism may project from the first and/or second member.

Another aspect of the invention provides a method of securing a suture in a suture retainer, including the following steps: providing a suture retainer having a retainer body and a plurality of suture attachment mechanisms spaced circumferentially about the retainer body; and attaching a suture strand to the retainer body at each of the suture attachment mechanisms. In some embodiments, each suture attachment mechanism is at least a pair of teeth, with the method further including the step of inserting the suture strand between each of the pairs of teeth. The method may also include the step of releasing the suture strand from the suture attachment mechanisms after the attaching step and possibly the step of reattaching the suture strand to the suture attachment mechanisms after the releasing step.

In some embodiments the method also includes the step of contacting the suture strand with a suture guide to maintain an angle between the suture strand and one of the suture attachment mechanisms. The contacting step may include the step of contacting with the suture guide a portion of the suture strand between a point where the suture strand leaves a tissue surface and a point where the suture strand contacts a suture attachment mechanism.

In some embodiments, the attaching step includes the step of attaching a needle-end of the suture strand to needle-end suture attachment mechanisms, with the method further including the step of attaching a non-needle-end of the suture strand to the suture retainer. The retainer body may include a first member and a second member, and the step of attaching the non-needle-end of the suture strand may include the step of inserting at least a portion of the second member into the first member to hold the non-needle-end of the suture strand. In embodiments in which the retainer body has a movable connection between the first member and the second member, the inserting step may include the step of moving the second member about the movable connection with respect to the first member and possibly the step of snapping the first and second members together.

Yet another aspect of the invention provides a suturing method including the steps of: attaching a first end of a suture strand to a suture retainer; contacting a tissue contact portion of the suture strand with tissue to be sutured, the tissue contact portion being disposed between the first end of the suture strand and a second end of the suture strand; and attaching the second end of the suture strand to the suture retainer at a plurality of suture attachment points spaced circumferentially about the suture retainer. In some embodiments, the step of attaching the second end of the suture strand includes the step of placing the second end of the suture strand between a plurality of pairs of teeth, each pair of teeth being disposed at one of the suture attachment points. The method may also include the step of detaching the suture strand from the suture attachment mechanisms after the attaching step and possibly the step of reattaching the suture strand to the suture attachment mechanisms after the detaching step.

In some embodiments, the step of attaching the first end of the suture strand includes the step of inserting at least a portion of a first suture retainer body member into a second suture retainer body member. The attaching step may also include the step of placing the first end of the suture strand into a slot formed in the first suture retainer body member. The inserting step may include the step of aligning the first suture retainer body member with the second suture retainer body member, such as by rotating the second body member to align a second suture retainer body member alignment element with a first suture retainer body member alignment element.

Some embodiments of this aspect of the invention include the step of contacting the second end of the suture strand with a suture guide to maintain an angle between the suture strand and one of suture attachment mechanisms, such as by making a first contact of the second end of the suture strand with the suture retainer.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

FIGS. 1-7 show embodiments of a suture retainer 10 with two principal parts: a wheel portion 12 and a plug portion 14. Wheel portion 12 has sets of teeth 16 arranged around its circumference. As shown best in FIG. 7, tooth sets 16 each have a pair of inclined facing edges 18 and 20 that diverge from the center of wheel portion 12 toward the outer circumference of wheel portion 12. The spacing and angle of inclined surfaces 18 and 20 are chosen to engage the diameter of the suture strand with which the retainer is intended to be used. In one embodiment, for example, the angle between the inclined surfaces of each tooth set is about 10° or less.

In the embodiments shown in FIGS. 1-7, wheel portion 12 has three sets of teeth arranged about the circumference of wheel portion 12 in a manner to produce pull angles of between about 50° and 70° for each tooth set. Pull angle is defined as the angle formed on the "pull" side of the tooth set between a suture held by the tooth set and a line normal to a plane formed by the juxtaposed edges of the teeth. The tooth sets extend radially from the center of wheel portion 12 or may extend on an angle from a radius in order to provide the desired pull angle. In other embodiments, the suture retainer may have one, two or more than three sets of suture attachment mechanisms, such as the teeth shown in the embodiments of FIGS. 1-7.

A pair of plates or flanges 22 and 24 surround and support the tooth sets. Plates 22 and 24 also aid the surgeon in passing the needle end of the suture around wheel portion 12 to engage successive tooth sets. Wheel portion 12 has a central opening 26 and an alignment hole 28. Opening 26 and hole 28 mate with corresponding portions of plug portion 14 when the suture retainer is assembled.

Plug portion has lock arms 30 and 32 extending from a plate 34. Lock arms 30 and 32 have cam surfaces 36 and 38, respectively that are adapted to bend arms 30 and 32 inward when surfaces 36 and 38 engage the edges of opening 26 in wheel portion 12. A slot 40 is formed between arms 30 and 32.

Also extending from plate 34 is a suture guide mechanism (such as hook 42 in FIG. 1 or tab 50 in FIG. 7) and an alignment member 44. Alignment member 44 extends into alignment hole 28 when plug portion 14 is connected to wheel portion 12. This arrangement sets the position of the suture guide mechanism (e.g., hook 42) with respect to one of the tooth sets 16 so that hook may serve as a retainer or guide for a suture strand as it enters a first tooth set 16, as described below. Other means of aligning the plug and wheel portions of the suture retainer may be used, of course, without departing from the invention.

Figure 1:
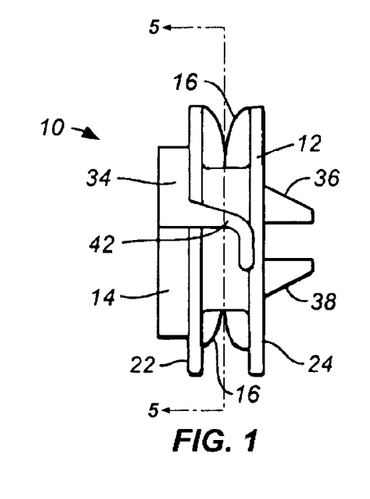
FIG. 1 is a side elevational view of a suture retainer according to one embodiment of this invention.
Figure 2:
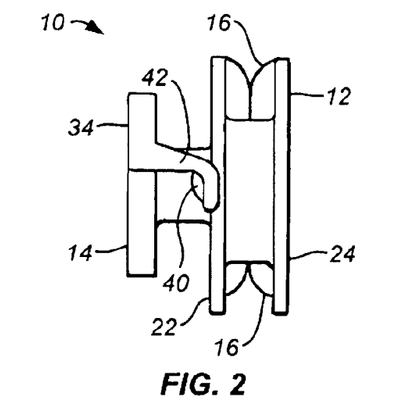
FIG. 2 is a side elevational view of the suture retainer of FIG. 1, partially assembled.
Figure 3:
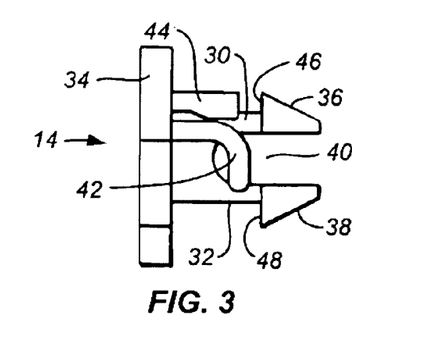
FIG. 3 is a side elevational view of a plug portion of the suture retainer of FIG. 1.
Figure 4:
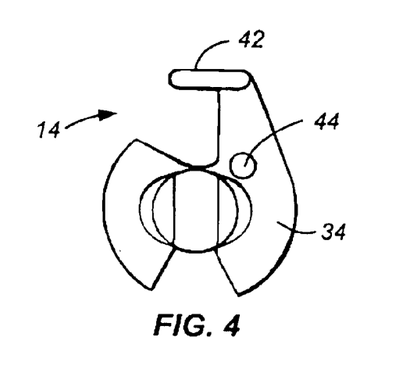
FIG. 4 is a top elevational view of the plug portion of the suture retainer shown in FIG. 3.
Figure 5:
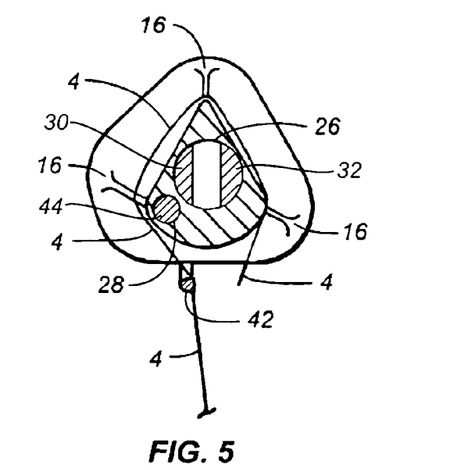
FIG. 5 is a medial cross-sectional view taken along line 5-5 of the embodiment of the suture retainer of FIG. 1 with a suture strand laid into the attachment mechanisms.
Figure 6:
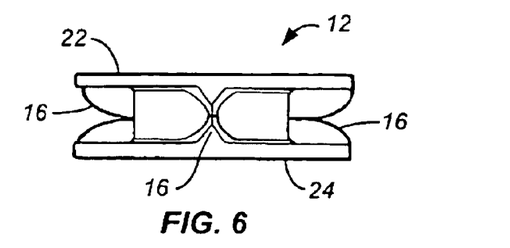
FIG. 6 is a side elevational view of the wheel portion of the suture retainer shown in FIG. 1.
Figure 7:
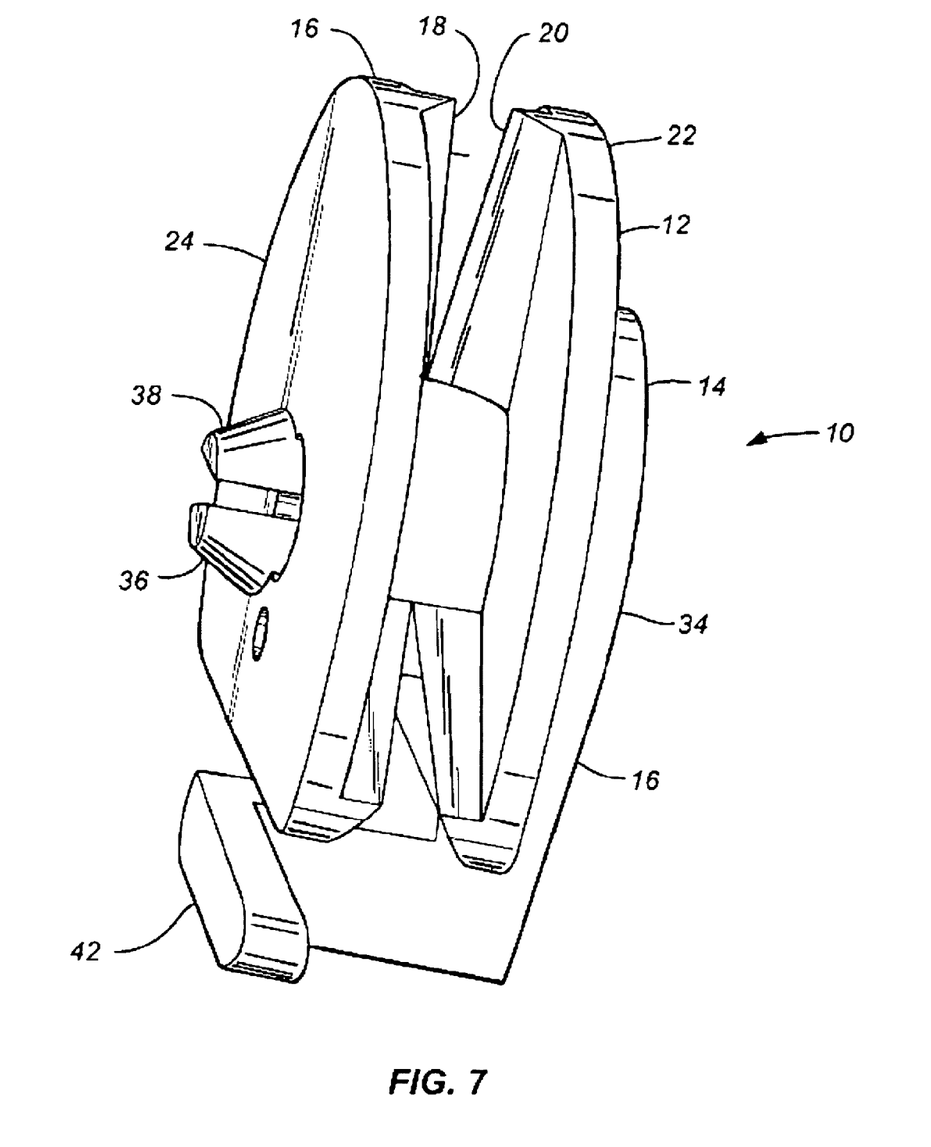
FIG. 7 is a perspective view of the suture retainer shown in FIG. 1.

To use the suture retainer, the non-needle-end of a suture is inserted into the slot 40, preferably when the suture retainer is in the partially assembled configuration shown in FIG 2. Plug portion 14 is then advanced completely into wheel portion 12, with alignment member 44 aligned with alignment hole 28. As lock arms 30 and 32 move into opening 26, cam surfaces 36 and 38 engage the edges of opening 26 to move arms 30 and 32 inward. After cam surfaces 36 and 38 have completely passed through opening 26, arms 30 and 32 move outwardly so that lock surfaces 46 and 48 formed on arms 30 and 32, respectively, engage the far side of plate 24 in a snap connection, as shown in FIGS. 1 and 7, and the suture strand is gripped firmly, preferably in a controlled clearance space between the shaft of the plug and the bore of the wheel.

Figure 8:
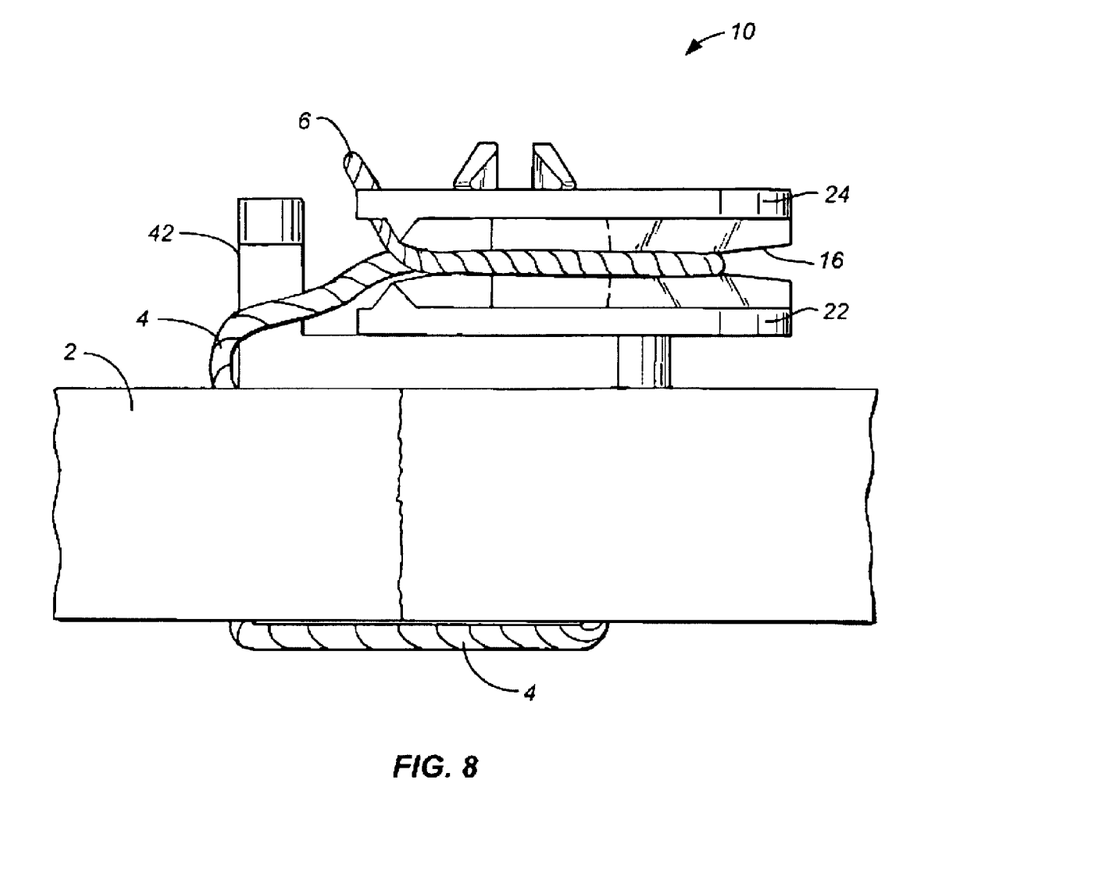
FIG. 8 shows a suture retainer according to one embodiment of this invention in use to retain a suture strand.

When thus assembled, the non-needle-end of the suture strand is held firmly by suture retainer 10. The surgeon can then pass the needle and needle-end of the suture strand through and/or around the tissue 2 to be sutured or ligated, pulling suture retainer 10 against the surface of the tissue, as shown in FIG. 8. When the suture stitch is complete, the surgeon passes the needle-end 6 of the suture strand 4 around and in engagement with the suture guide mechanism 42, tensions the stitch, then guides the needle-end of the suture strand in succession into the three sets of teeth 16, maintaining the tension in the suture strand as the surgeon progresses. If the stitch tension and suture retainer grip are satisfactory, the surgeon then may sever the unused ends of the suture strand. If, however, the stitch needs to be retensioned to either increase or decrease tissue approximation or the retainer grip needs to be adjusted, the surgeon may pull the suture strand away from the tooth sets, then retension the stitch and reengage the suture strand with the suture retainer. While the illustrations show a clockwise wrapping of the suture, other embodiments of the invention may employ counterclockwise wrapping of the suture around the retainer.

The shape and position of hook 42 help retain the suture strand's orientation and pull angle with respect to the first set of teeth 16 it encounters. In addition, the curved end of hook 42 helps retain the suture strand in place after the suturing procedure has been completed. Other shapes and manners of suture strand guides may be used in place of hook 42, such as tabs, posts, rings, etc. In addition, the suture strand guide of this invention may be used with suture retainers having one, two or more than three suture attachment mechanisms.

Figure 9:
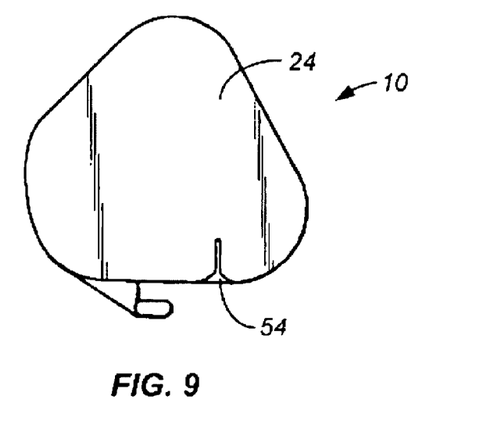
FIG. 9 is a top elevational view of a suture attachment feature that may be used with embodiments of this invention.
Figure 10:
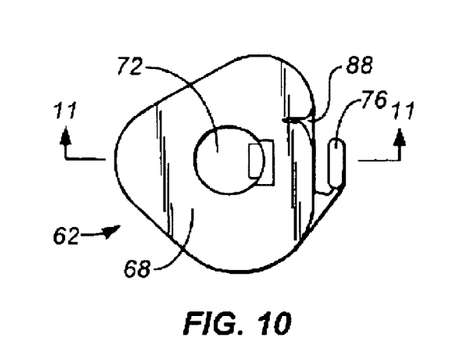
FIG. 10 is a top elevational view of the wheel portion of yet another embodiment of the suture retainer of this invention.

FIG. 9 shows an optional feature for holding the far end of the needle-end of the suture strand after engagement with the retainer's sets of teeth. A slot 54 is formed in plate 24 of suture retainer 10. The end of the suture strand may be placed within slot 54 to provide additional retention of the suture and to maintain the retention of the suture provided by the last set of teeth before severing and removing the needle end of the suture. The slot may be tapered or parallel, as shown, and may be used with any of the embodiments of this invention. This feature may also be used to retain one end of a suture strand without regard to whether, or the manner in which, the other end of the suture strand is retained.

Another embodiment of the invention is shown in FIGS. 10-13. Suture retainer 60 has a wheel portion 62 and a plug portion 64. Like the previous embodiments, wheel portion 62 has sets of teeth 66 arranged about a circumference of wheel portion 62. A pair of plates or flanges 68 and 70 surround and support the tooth sets. Wheel portion 62 also has a central opening 72 with a movable member 74 formed inside the opening. A suture guide mechanism 76 extends from wheel portion 62.

Figure 11:
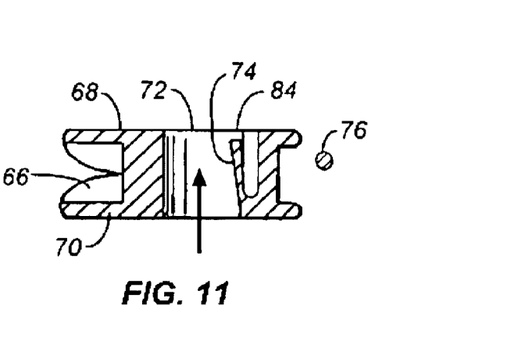
FIG. 11 is a cross-sectional view taken along the line A-A of FIG. 10.
Figure 12:
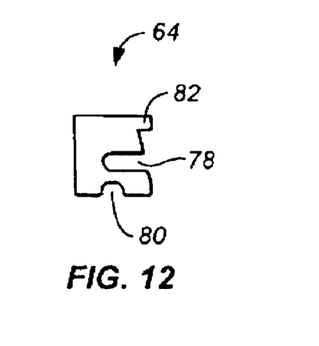
FIG. 12 is a side elevational view of the plug portion of the embodiment of FIG. 10.
Figure 13:
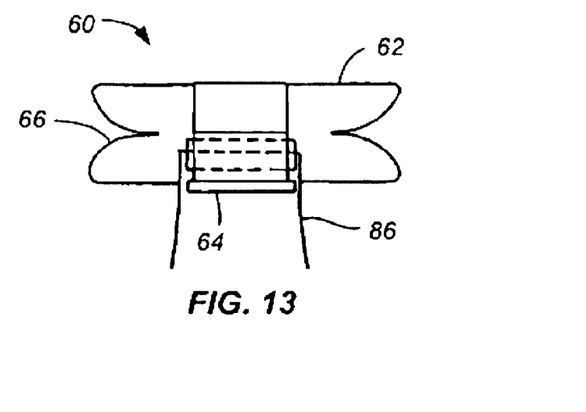
FIG. 13 is a schematic view of an assembled suture retainer according to the embodiment of FIGS. 10-12 showing a suture in place.
Figure 14:
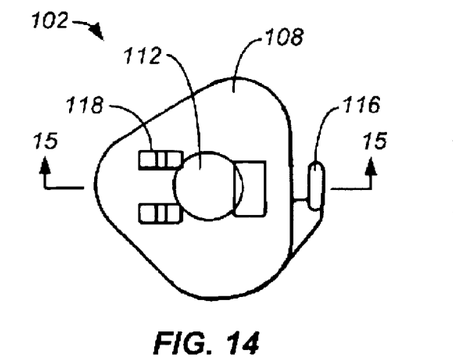
FIG. 14 is a top elevational view of the wheel portion of another embodiment of the suture retainer of this invention.
Figure 15:
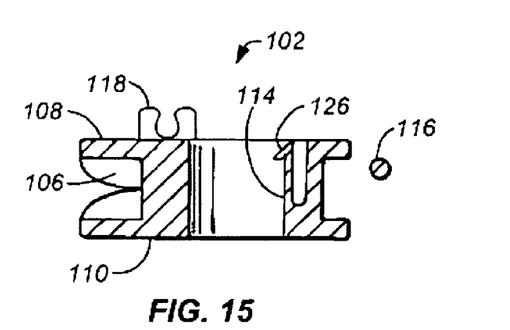
FIG. 15 is a cross-sectional view taken along the line A-A of FIG. 14.
Figure 16:
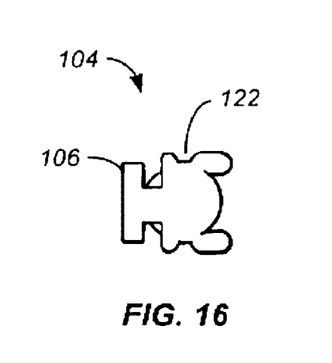
FIG. 16 is a top elevational view of the plug portion of the embodiment of FIG. 14.

Plug portion 64 has a slot 78 and a groove 80. A tab 82 extends from the top surface of plug portion 64. Prior to insertion (or after partial insertion) of plug 64 into wheel 62 in the direction shown by the arrow in FIG. 11, the non-needle-end of a suture strand 86 may be inserted into slot 78 and, if desired, wrapped around groove 80 and back through slot 78. Plug 64 is then inserted fully into opening 72 of wheel 62 from the bottom, as shown in FIG. 11. As it is inserted, the plug's tab 82 pushes the top of the wheel's movable member 74 radially away from the center of opening 72. When the plug's tab 82 reaches a space 84 above movable member 74, movable member 74 moves back toward the center of opening 72, snapping plug 64 in place within wheel 62. In this position, the non-needle-end of suture strand 86 is held firmly by suture retainer 60. The suture thread may be tensioned downward, as shown in FIG. 13.

After assembly of the suture retainer, the surgeon may then use the needle-end of the suture to perform the suturing or ligation procedure. As in the other embodiments, when the suture stitch is complete, the surgeon passes the needle-end of the suture strand around the suture guide 76, then inserts the suture strand in succession into the sets of teeth 66. Thereafter, the surgeon may place the needle-end of the suture strand into a slot 88 formed in plate or flange 68.

In the embodiment shown in FIGS. 10-13, the top and bottom edges of plug 64 lie flush with the top and bottom edges of wheel 62. This arrangement is an optional feature of the invention. Also, it should be understood that other suture attachment mechanisms and other numbers of suture attachment mechanisms may be used in the suture retainer of this invention.

FIGS. 14-17 show yet another embodiment of this invention. Suture retainer 100 has a wheel portion 102 and a plug portion 104. Like the previous embodiments, wheel portion 102 has sets of teeth 106 arranged about a circumference of wheel portion 102. A pair of plates or flanges 108 and 110 surround and support the tooth sets. Wheel portion 102 also has a central opening 112 with a movable arm 114 formed inside the opening. A suture guide mechanism 116 extends from wheel portion 112.

Plug portion 104 has a pair of pins 107 extending from an upper surface. When the suture retainer is assembled prior to use, pins 107 are snapped into openings formed by pairs of arms 118 extending upward from the upper surface of flange 108 of wheel 102 to form a hinge to allow rotational movement between plug 104 and wheel 102. Other forms of movable connection between the plug and wheel are also covered by this invention.

Figure 17:
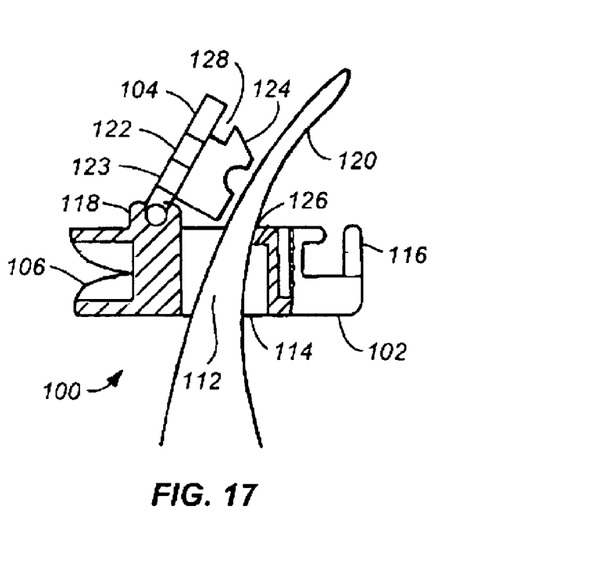
FIG. 17 is a cross-sectional view of a suture and a partially assembled suture retainer according to the embodiment of FIGS. 14-16, prior to use.

FIG. 17 shows the arrangement of plug 104 and wheel 102 prior to use of the suture retainer. A loop 120 formed in the non-needle-end of a suture strand is passed up through opening 112. The suture strand may then be wrapped one or more times around plug 104 with the suture strand lying in grooves 122 (and groove 123, for multiple suture wraps) formed in plug 104. Plug 104 is then rotated downward about the hinge formed by pins 107 and arms 118. As the bottom of plug 104 enters opening 112, an angled surface 124 of plug 104 engages an angled surface formed on the top of a tab 126 of movable arm 114, pushing the top of arm 114 radially outward. When plug 104 has been completely inserted into wheel 102, tab 126 moves radially inward into a slot 128 formed in plug 104 to latch plug 104 in place within wheel 102. The surgeon may then use the needle-end of the suture to perform the suturing or ligation procedure. As in the other embodiments, when the suture stitch is complete, the surgeon passes the needle-end of the suture strand around the suture guide 116, then inserts the suture strand in succession into the sets of teeth 106 to hold the suture in place.

The use of circumferentially spaced tooth sets provides multiple suture attachment mechanisms each at desired pull angles. This arrangement reduces the likelihood of slippage of the suture strand in the event one of the attachment points fails or provides less than 100% of the required tensioning force. Other numbers of tooth sets set at other pull angles may also be used. In addition, other attachment mechanisms may be used in place of the tooth sets described above, such as high friction surfaces, hooks, posts, rings, etc.

The components of the device described above can be made of medically suitable metal or plastics, including bioabsorbable polymers. Example materials include stainless steel, polycarbonate and polyglycolide.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A suture retainer comprising a retainer body, the retainer body comprising:
    a wheel portion including a substantially planar first flange and a substantially planar second flange, the first flange and the second flange defining an outer circumference of the wheel portion and the first flange being spaced from the second flange about the outer circumference, thereby forming an outward radially open channel throughout the outer circumference, and at least three suture attachment mechanisms spaced circumferentially about the retainer body between the first flange and the second flange, wherein each of the suture attachment mechanisms is adapted to hold a suture strand at a discrete attachment point, and further wherein the wheel portion includes a first aperture extending therethrough substantially perpendicular to the first flange and the second flange, and the wheel portion includes an alignment aperture extending therethrough spaced from and substantially parallel to the first aperture;
    a plug portion adapted to cooperate with the aperture in the wheel portion, the plug portion comprising,
        a plate;
        a pair of lock arms coupled to the plate, each lock arm having a distal end extending away from the plate in a first direction;
        an alignment peg extending away from the plate in the first direction;
        a slot disposed between the lock arms; and,
        a cam surface on each lock arm, each cam surface extending from the distal end of the lock arm on which the cam surface is situated,
    wherein both cam surfaces contact the first aperture in the wheel portion upon insertion of the lock arms into the first aperture to cause the lock arms to bend at least partially into the slot,
    wherein the alignment peg and the alignment aperture form an alignment mechanism adapted to orient the plug portion with respect to the wheel portion, wherein the alignment mechanism at least substantially prevents rotation of said plug portion with respect to said wheel portion.

2. The suture retainer of claim 1 wherein each suture attachment mechanism comprises at least a pair of teeth.

3. The suture retainer of claim 2, each pair of teeth comprising a pair of inclined facing edges that diverge from a medial section of the wheel portion toward the outer circumference of the wheel portion.

4. The suture retainer of claim 3, the inclined facing edges of at least one pair of teeth forming an angle of less than or equal to ten degrees.

5. The suture retainer of claim 1 wherein each suture attachment mechanism is adapted to releasably hold the suture strand.

6. The suture retainer of claim 5 wherein each suture attachment mechanism releasably holds the suture strand independent of the releasable hold of the suture strand by the other suture attachment mechanisms.

7. The suture retainer of claim 1 further comprising a suture guide mechanism adapted to maintain an angle between the suture strand and one of the suture attachment mechanisms.

8. The suture retainer of claim 7 wherein the suture guide mechanism comprises a projection from the retainer body.

9. The suture retainer of claim 8 wherein the suture guide mechanism projects from the wheel portion.

10. The suture retainer of claim 8 wherein the suture guide mechanism projects from the plug portion.

11. The suture retainer of claim 10
    wherein the suture guide mechanism comprises a projection from the perimeter of the plate, the projection including a hooked portion spaced from the wheel portion.

12. The suture retainer of claim 7 wherein the suture guide mechanism comprises a projection from the perimeter of the retainer body, the projection including a hooked portion spaced from the wheel portion.

13. The suture retainer of claim 1 wherein the plug portion is movable with respect to the wheel portion.

14. The suture retainer of claim 1 further comprising a snap connection between the plug portion and the wheel portion.

15. The suture retainer of claim 1 wherein the at least three suture attachment mechanisms are substantially equally disposed around the first aperture.

* * * * *